US012797021B2

(12) United States Patent
Hayashi

(10) Patent No.: US 12,797,021 B2
(45) Date of Patent: Nov. 17, 2026

(54) X-RAY CT APPARATUS COMPRISING A PLURALITY OF DETECTOR MODULES

(71) Applicant: FUJIFILM Corporation, Tokyo (JP)

(72) Inventor: Tatsuhiko Hayashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 162 days.

(21) Appl. No.: 18/902,800

(22) Filed: Sep. 30, 2024

(65) Prior Publication Data

US 2025/0107761 A1 Apr. 3, 2025

(30) Foreign Application Priority Data

Oct. 3, 2023 (JP) ................................ 2023-171891

(51) Int. Cl.
*A61B 6/03* (2006.01)
*A61B 6/00* (2006.01)
*A61B 6/42* (2024.01)
*G01T 1/20* (2006.01)

(52) U.S. Cl.
CPC ............ *A61B 6/4266* (2013.01); *A61B 6/032* (2013.01); *A61B 6/4233* (2013.01); *A61B 6/54* (2013.01); *G01T 1/20182* (2020.05); *G01T 1/20184* (2020.05); *G01T 1/20186* (2020.05); *G01T 1/20187* (2020.05); *G01T 1/20188* (2020.05); *G01T 1/20189* (2020.05); *G01T 1/2019* (2020.05)

(58) Field of Classification Search
CPC ........... A61B 6/032; A61B 6/035; A61B 6/42; A61B 6/4208; A61B 6/4233; A61B 6/4241; A61B 6/4258; A61B 6/4266; A61B 6/4275; A61B 6/52; A61B 6/5205; A61B 6/54; A61B 6/542; A61B 6/545; G01T 1/2018; G01T 1/20182; G01T 1/20184; G01T 1/20186; G01T 1/20187; G01T 1/20188; G01T 1/20189; G01T 1/2019
USPC ........................................ 250/370.09; 378/19
See application file for complete search history.

(56) References Cited

U.S. PATENT DOCUMENTS 6,396,898 B1 * 5/2002 Saito .................... G01N 23/046 378/19
6,510,195 B1 * 1/2003 Chappo ............... G01T 1/20182 250/370.09
6,587,538 B2 * 7/2003 Igarashi ............... A61B 6/4291 378/19
6,671,345 B2 * 12/2003 Vrettos .................. A61B 6/032 378/19

(Continued)

*Primary Examiner* — Allen C. Ho
(74) *Attorney, Agent, or Firm* — JCIPRNET

(57) ABSTRACT

An X-ray CT apparatus includes: an X-ray source that irradiates a subject with X-rays; an X-ray detector that detects the X-rays transmitted through the subject; a signal processing unit that obtains a plurality of projection data based on an electric signal output from the X-ray detector; and an image generation unit that generates a tomographic image by using the projection data, in which the X-ray detector includes a plurality of detector modules that are arranged in a channel direction, the detector module includes sub-detector modules that are arranged in a body axis direction of the subject, and the sub-detector module is configured such that a plurality of tiling modules that convert the X-rays into an electric signal are associated with one collimator that removes scattered rays.

7 Claims, 5 Drawing Sheets

(56) References Cited

U.S. PATENT DOCUMENTS

| | | | | |
|---|---|---|---|---|
| 6,982,424 | B2 * | 1/2006 | Vafi | G01T 1/2018<br>250/370.11 |
| 7,196,331 | B2 * | 3/2007 | Heismann | A61B 6/032<br>250/367 |
| 8,548,119 | B2 * | 10/2013 | Ikhlef | G01T 1/20182<br>378/19 |
| 8,824,635 | B2 * | 9/2014 | Tkaczyk | A61B 6/037<br>250/370.09 |
| 8,873,705 | B2 * | 10/2014 | Konno | A61B 6/032<br>378/19 |
| 9,320,476 | B2 * | 4/2016 | Iso | A61B 6/4291 |
| 9,480,446 | B2 * | 11/2016 | Hashimoto | G01T 1/20185 |
| 9,519,069 | B2 * | 12/2016 | Lacey | A61B 6/032 |
| 9,835,733 | B2 * | 12/2017 | Ying | G01T 1/20182 |
| 9,910,165 | B2 * | 3/2018 | Yu | A61B 6/032 |
| 10,307,117 | B2 * | 6/2019 | Park | A61B 6/4266 |
| 10,531,848 | B2 * | 1/2020 | Ikhlef | G01T 1/20182 |
| 10,588,593 | B2 * | 3/2020 | Yamazaki | A61B 6/4208 |
| 11,020,072 | B2 * | 6/2021 | Narayanaswamy | G01T 1/2018 |
| 11,166,685 | B2 * | 11/2021 | Takayasu | G01T 1/20182 |
| 11,197,643 | B2 * | 12/2021 | Gregerson | A61B 6/035 |
| 11,510,637 | B2 * | 11/2022 | Nishijima | A61B 6/4291 |
| 11,523,783 | B2 * | 12/2022 | Hayashi | G01T 1/20182 |
| 11,602,317 | B2 * | 3/2023 | Ikhlef | G01T 1/20182 |
| 12,181,616 | B2 * | 12/2024 | Nishijima | G01T 1/243 |
| 12,588,879 | B2 * | 3/2026 | Nakagawa | A61B 6/4241 |
| 2016/0170038 | A1 | 6/2016 | Yu | |

* cited by examiner

X-RAY CT APPARATUS COMPRISING A PLURALITY OF DETECTOR MODULES

CLAIM OF PRIORITY

The present application claims priority from Japanese Patent Application JP 2023-171891 filed on Oct. 3, 2023, the content of which is hereby incorporated by reference into this application.

BACKGROUND OF THE INVENTION

1. Field of the Invention

The present invention relates to an X-ray detector mounted on an X-ray computed tomography (CT) apparatus.

2. Description of the Related Art

The X-ray CT apparatus is an apparatus that generates a tomographic image of a subject by using a plurality of projection data obtained by detecting X-rays transmitted through the subject from various directions. The tomographic image generated by the X-ray CT apparatus is used as a medical image for diagnosing the subject. In the X-ray CT apparatus, an X-ray detector is multi-sliced in a body axis direction of the subject to enable wide-range imaging in a short time.

US2016/0170038A discloses that, in order for the X-ray detector to be multi-sliced in the body axis direction of the subject, components in which a collimator that removes scattered rays and a tiling module that converts X-rays into an electric signal are in one-to-one correspondence are arranged in the body axis direction of the subject.

SUMMARY OF THE INVENTION

However, in US2016/0170038A, sufficient consideration is not given to manufacturing man-hours in a case where the X-ray detector is further multi-sliced. In a case where the components in which the collimator and the tiling module are in one-to-one correspondence are arranged in the body axis direction of the subject, it is necessary to align the number of collimators corresponding to the number of tiling modules, which increases the manufacturing man-hours.

An object of the present invention is to provide an X-ray CT apparatus capable of reducing manufacturing man-hours of an X-ray detector that is multi-sliced in a body axis direction of a subject.

In order to achieve the above object, according to an aspect of the present invention, there is provided an X-ray CT apparatus comprising: an X-ray source that irradiates a subject with X-rays; an X-ray detector that detects the X-rays transmitted through the subject; a signal processing unit that obtains a plurality of projection data based on an electric signal output from the X-ray detector; and an image generation unit that generates a tomographic image by using the projection data, in which the X-ray detector includes a plurality of detector modules that are arranged in a channel direction, the detector module includes sub-detector modules that are arranged in a body axis direction of the subject, and the sub-detector module is configured such that a plurality of tiling modules that convert the X-rays into an electric signal are associated with one collimator that removes scattered rays.

According to the present invention, it is possible to provide an X-ray CT apparatus capable of reducing manufacturing man-hours of an X-ray detector that is multi-sliced in a body axis direction of a subject.

DESCRIPTION OF THE PREFERRED EMBODIMENTS

Figure 1:
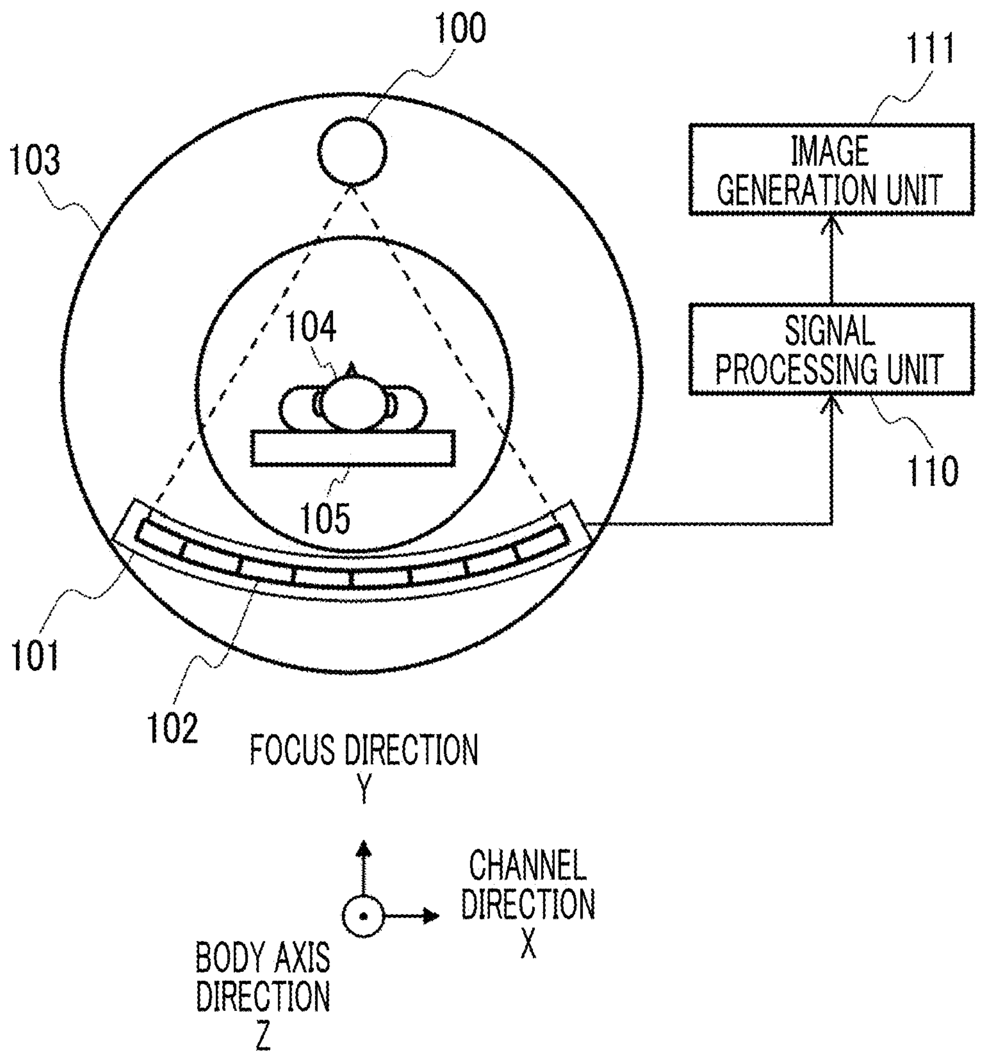
FIG. 1 is a diagram showing an overall configuration of an X-ray CT apparatus.

Hereinafter, examples of an X-ray CT apparatus according to an embodiment of the present invention will be described with reference to the accompanying drawings. In the following description and the accompanying drawings, components having the same functional configuration will be denoted by the same reference numerals, and duplicated descriptions will not be repeated.

Example 1

An overall configuration of an X-ray CT apparatus will be described with reference to FIG. 1. The X-ray CT apparatus comprises an X-ray source 100, an X-ray detector 101, a rotation plate 103, a table 105, a signal processing unit 110, and an image generation unit 111.

The X-ray source 100 is a device that irradiates a subject 104 with X-rays and is, for example, an X-ray tube device. The X-rays applied from the X-ray source 100 are radially emitted from a focus of the X-ray source 100.

The X-ray detector 101 is a device detecting the X-rays transmitted through the subject 104, converts the X-rays into an electric signal, and transmits the electric signal to the signal processing unit 110. The X-ray detector 101 comprises a plurality of detector modules 102 that are arranged in a channel direction. A configuration of the detector module 102 will be described below with reference to FIGS. 2A and 2B. In the X-ray detector 101, a direction toward the focus of the X-ray source 100 is defined as a Y direction, a body axis direction of the subject 104 is defined as a Z direction, and a channel direction, which is a direction orthogonal to both the Y direction and the Z direction, is defined as an X direction.

The rotation plate 103 is a device that mounts the X-ray source 100 and the X-ray detector 101 and rotates. The X-rays that transmit through the subject 104 are detected from various directions by the rotation of the rotation plate 103.

The table 105 is a device on which the subject 104 is placed and moves the subject 104 in the body axis direction or a direction orthogonal to a body axis of the subject 104.

The signal processing unit 110 is a device that controls each unit and receives the electric signal transmitted from the X-ray detector 101, and is, for example, a microprocessing unit (MPU). The signal processing unit 110 obtains a plurality of projection data based on the received electric signal and transmits the obtained projection data to the image generation unit 111.

The image generation unit 111 is a device that generates a tomographic image using the plurality of projection data transmitted from the signal processing unit 110, and is, for example, a graphics processing unit (GPU). The tomographic image generated by the image generation unit 111 is displayed on a display device such as a liquid crystal display and is used as a medical image for diagnosing the subject 104.

Figure 2A:
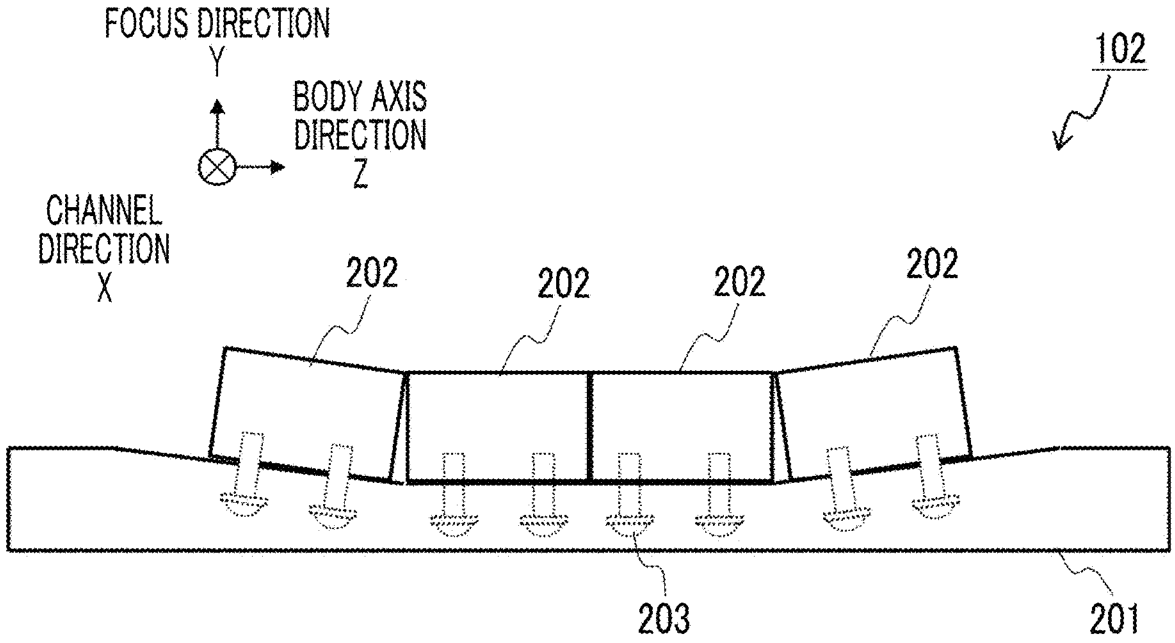
FIG. 2A is a diagram showing an example of a configuration of a detector module.
Figure 2B:
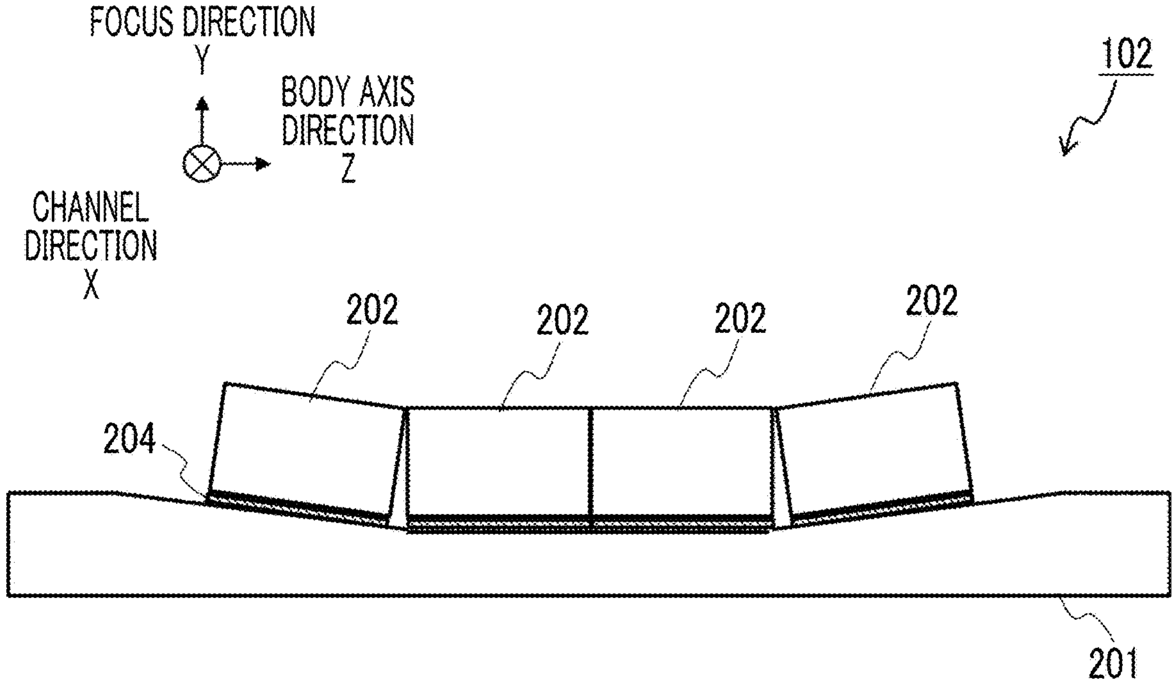
FIG. 2B is a diagram showing another example of the configuration of the detector module.

The detector module 102 will be described with reference to FIGS. 2A and 2B. The detector module 102 comprises a plurality of sub-detector modules 202 and a support block 201.

The plurality of sub-detector modules 202 are arranged along the body axis direction of the subject 104 and are fixed on the support block 201. In addition, it is preferable that the sub-detector modules 202 are disposed such that their upper surfaces face the focus of the X-ray source 100. A configuration of the sub-detector module 202 will be described below with reference to FIG. 3.

The support block 201 is a member that supports the plurality of sub-detector modules 202. The sub-detector module 202 is fixed by a screw 203 as shown in FIG. 2A, or the sub-detector module 202 is fixed by an adhesive 204 as shown in FIG. 2B. The screw 203 and the adhesive 204 may be used in combination. As will be described below, since the sub-detector module 202 serves as a heat source, a material having a relatively large thermal conductivity, for example, aluminum, is used for the support block 201 such that heat generated in the sub-detector module 202 can be dissipated. In addition, it is preferable that the adhesive 204 also has excellent thermal conductivity.

The sub-detector module 202 will be described with reference to FIG. 3. The sub-detector module 202 comprises a collimator 301, a substrate 303, and a plurality of tiling modules 302.

The tiling module 302 includes a scintillator 304, a photodiode 305, and an AD conversion unit 306. The scintillator 304 is a member converting X-rays into visible light and emits an amount of visible light corresponding to an amount of incident X-rays. The photodiode 305 is an element converting visible light into an electric signal and transmits an electric signal corresponding to an amount of incident visible light to the AD conversion unit 306. The electric signal that is transmitted to the AD conversion unit 306 is an analog signal. A plurality of detection elements are formed on an XZ plane of the scintillator 304 and the photodiode 305, and the analog signal is output for each detection element. The AD conversion unit 306 converts the analog signal transmitted from the photodiode 305 into a digital signal. In a case of converting the analog signal into the digital signal, since the AD conversion unit 306 generates heat, the sub-detector module 202, which includes the tiling module 302 having the AD conversion unit 306, serves as a heat source.

The substrate 303 is a member that supports the plurality of tiling modules 302. In order to dissipate the heat generated by the AD conversion unit 306 of the tiling module 302, a material having a relatively large thermal conductivity, for example, aluminum, is used for the substrate 303. In addition, for example, a thickness of the adhesive layer applied between the substrate 303 and the tiling module 302 may be adjusted such that X-ray incidence surfaces of the tiling modules 302 are flush with each other. The adhesive layer having a relatively large thermal conductivity is used.

The collimator 301 is a member removing scattered rays generated by the subject 104 or the like, includes a grid or a slit formed of a material having a relatively large atomic number, for example, tungsten, and is disposed on the X-ray source 100 side with respect to the tiling module 302. The grid made of tungsten may be formed using a three-dimensional printer. The collimator 301 is mounted on the plurality of tiling modules 302 such that a line connecting each of a plurality of detection elements provided in the tiling module 302 and the focus of the X-ray source 100 passes through a hole of the grid or a gap of the slit, and is fixed by an adhesive. FIG. 3 illustrates a state before one collimator 301 is mounted on four tiling modules 302.

Figure 3:
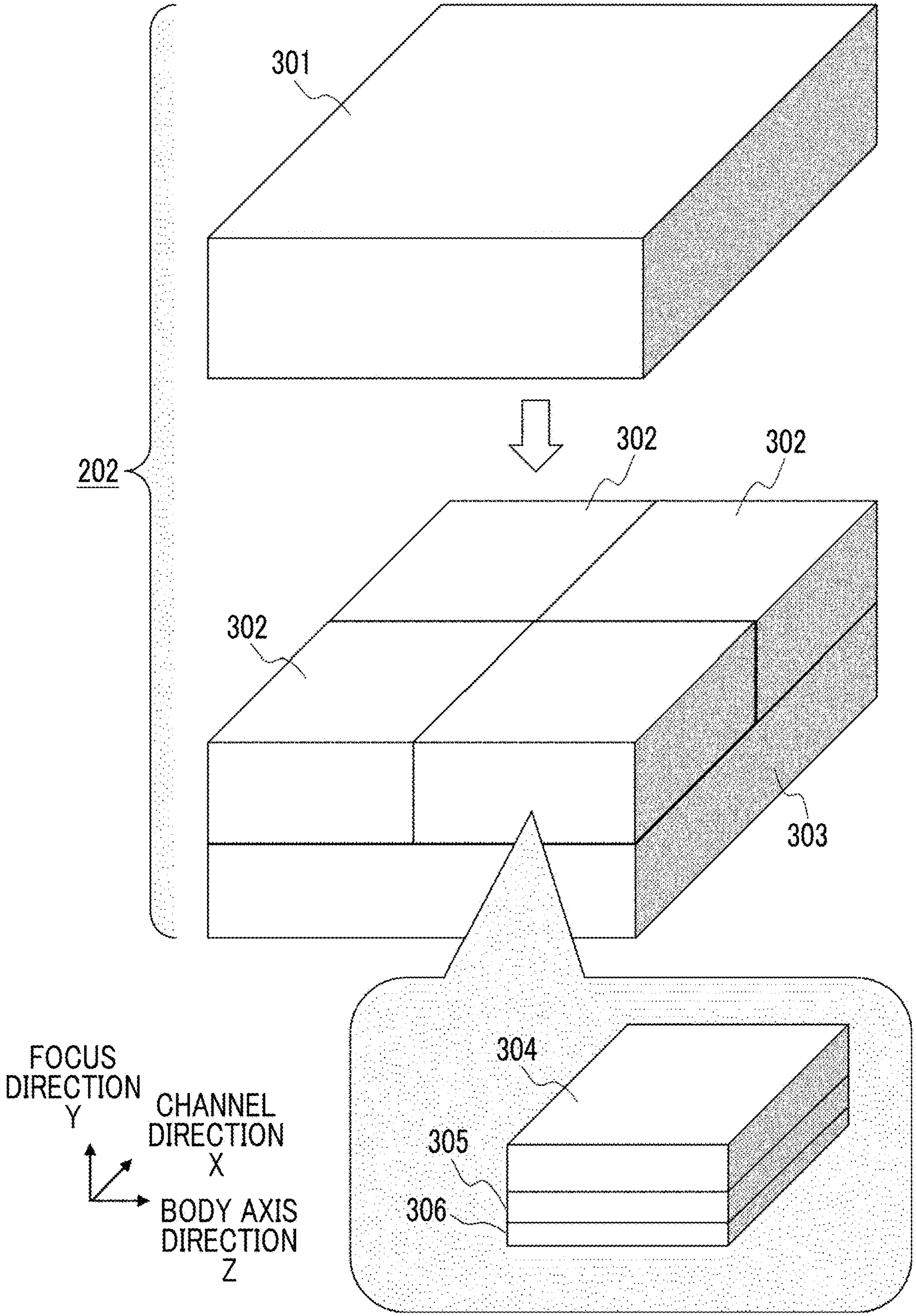
FIG. 3 is a perspective view showing an example of a configuration of a sub-detector module.

As illustrated in FIG. 3, the sub-detector module 202 is configured such that a plurality of tiling modules 302 are associated with one collimator 301. With such a configuration, even in a case where the X-ray detector 101 is further multi-sliced, the number of collimators 301 that require alignment can be suppressed, thereby reducing the manufacturing man-hours of the X-ray detector 101 that is multi-sliced in the body axis direction of the subject 104. The tiling module 302 may be arranged not only in two dimensions in the body axis direction and the channel direction as illustrated in FIG. 3, but also may be arranged only in the body axis direction or only in the channel direction.

Figure 4:
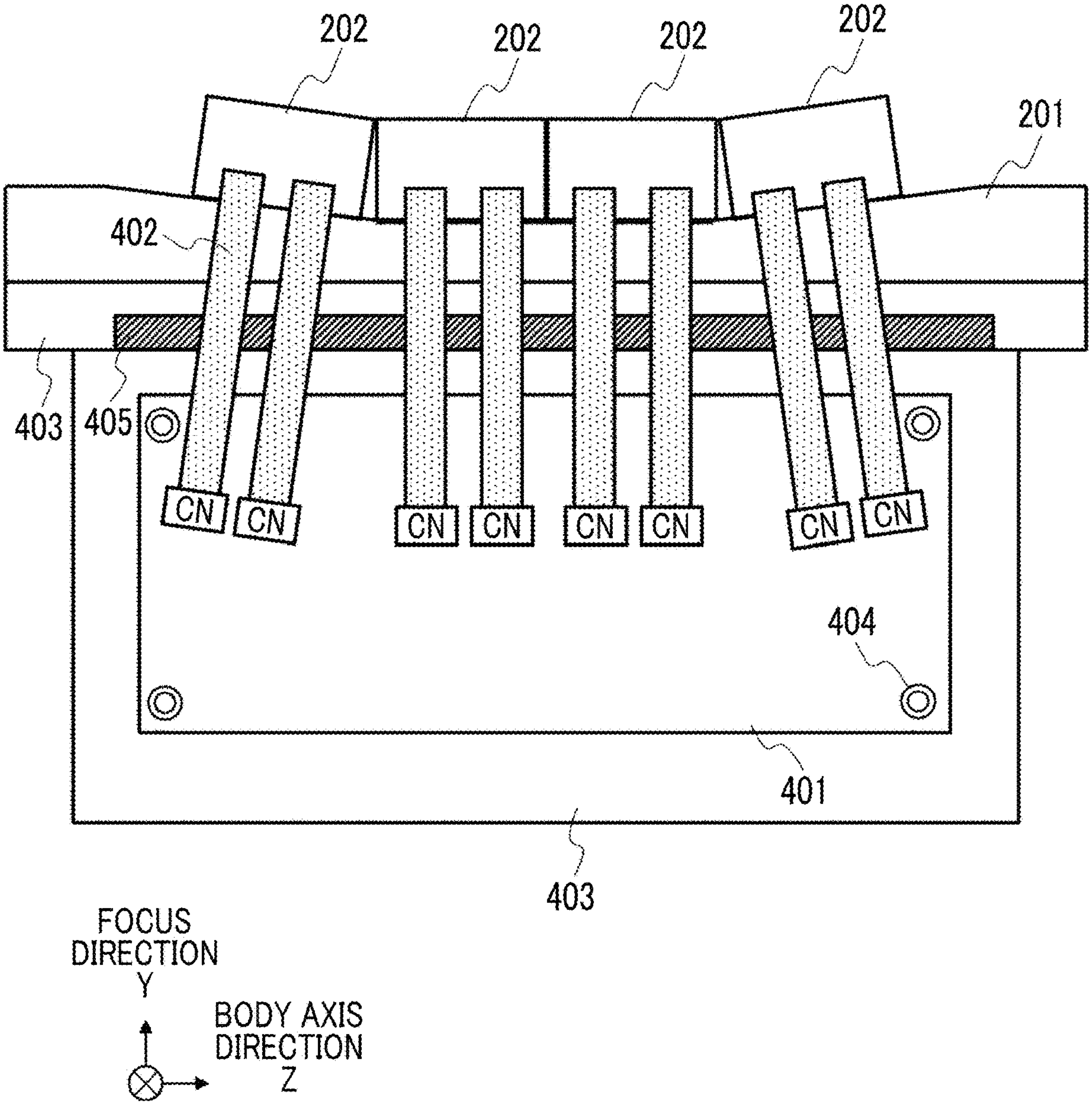
FIG. 4 is a diagram showing an example of a connection between the sub-detector module and a control board.
Figure 5:
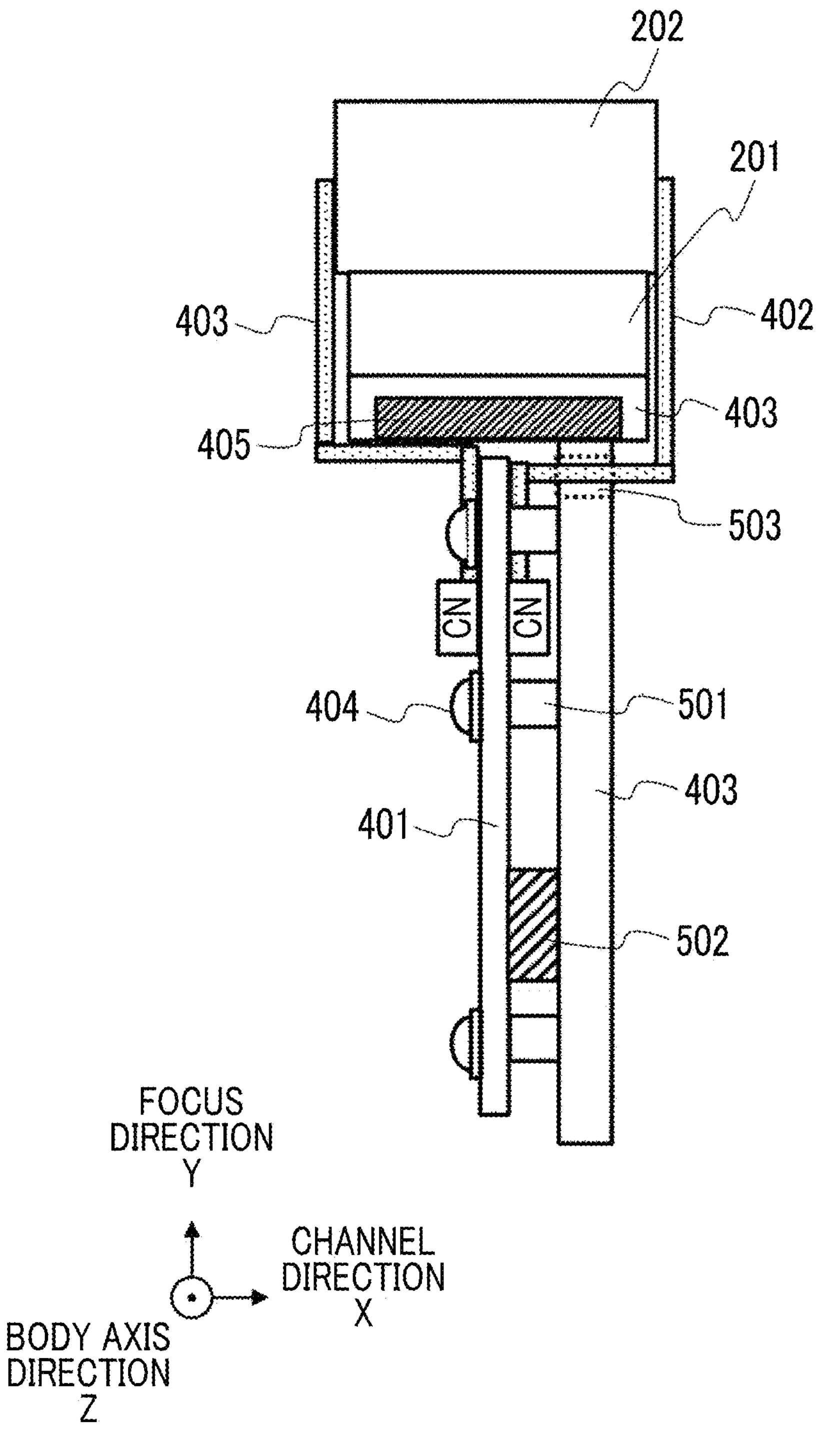
FIG. 5 is a diagram showing an example of a connection between the sub-detector module and the control board.

A connection between the sub-detector module 202 and the control board 401 will be described with reference to FIGS. 4 and 5. The control board 401 is a board that controls the AD conversion unit 306 provided in the sub-detector module 202. A flexible cable 402 is connected to each of the AD conversion units 306 of the sub-detector modules 202, and each of the flexible cables 402 is connected to a connector CN of the control board 401.

The control board 401 is fixed to a board attachment part 403 using a screw 404 or a stud 501. In addition, the board attachment part 403 may have a hole 503 for allowing the flexible cable 402 to pass through. As illustrated in FIG. 5, the board attachment part 403 has a T-shape in an XY plane, with the support block 201 disposed on an upper surface and the control board 401 fixed to a side surface. In order to dissipate the heat transmitted from the sub-detector module 202 via the support block 201, a material having a relatively large thermal conductivity, for example, aluminum, is used for the board attachment part 403. In addition, since the control board 401 serves as a heat source during operation, it is preferable that a heat conduction part 502 is provided between the control board 401 and the board attachment part 403. The board attachment part 403 is directly or indirectly connected to the rotation plate 103, and the heat transmitted to the board attachment part 403 is dissipated to the rotation plate 103.

In addition, in order to protect the control board 401 from X-rays, a shielding part 405 may be provided on the board attachment part 403. The shielding part 405 is made of a material having a relatively large atomic number, for example, lead, and is disposed to hide the control board 401 from the focus of the X-ray source 100. The disposition of the shielding part 405 is not limited to the example of FIG. 4 or FIG. 5, and, for example, the shielding part 405 may be disposed in a gap of the sub-detector modules 202. By restricting the disposition of the shielding part 405 to the gap of the sub-detector modules 202, it is possible to ensure heat dissipation properties and weight reduction of the board attachment part 403 while protecting the control board 401 from X-rays.

The examples of the present invention have been described above. The present invention is not limited to the above examples, and the components can be modified and embodied without departing from the spirit of the invention. In addition, a plurality of the components disclosed in the above examples may be combined as appropriate. Further, some components may be deleted from all the components shown in the above examples.

EXPLANATION OF REFERENCES

100: X-ray source
101: X-ray detector
102: detector module
103: rotation plate
104: subject
105: table
110: signal processing unit
111: image generation unit
201: support block
202: sub-detector module
203: screw
204: adhesive
301: collimator
302: tiling module
303: substrate
304: scintillator
305: photodiode
306: AD conversion unit
401: control board
402: flexible cable
403: board attachment part
404: screw
405: shielding part
501: stud
502: heat conduction part
503: hole
CN: connector

What is claimed is:

1. An X-ray CT apparatus comprising:

an X-ray source that irradiates a subject with X-rays;

an X-ray detector that detects the X-rays transmitted through the subject;

a signal processor that obtains a plurality of projection data based on an electric signal output from the X-ray detector; and an image processor that generates a tomographic image by using the plurality of projection data, wherein the X-ray detector includes a plurality of detector modules that are arranged in a channel direction, each detector module of the plurality of detector modules includes sub-detector modules that are arranged in a body axis direction of the subject, and each sub-detector module of the sub-detector modules includes a plurality of tiling modules that convert the X-rays into an electric signal and a collimator that removes scattered rays.

2. The X-ray CT apparatus according to claim 1, wherein each tiling module of the plurality of tiling modules includes an AD conversion unit that converts an analog signal into a digital signal, and each sub-detector module of the sub-detector modules further includes a substrate that supports the plurality of tiling modules, and the substrate includes a material having a relatively large thermal conductivity.

3. The X-ray CT apparatus according to claim 2, further comprising:

a control board that controls the AD conversion unit; and a board attachment part to which the control board is fixed, wherein the board attachment part includes a material having a relatively large thermal conductivity.

4. The X-ray CT apparatus according to claim 3, further comprising:

a shielding part that protects the control board from the X-rays is provided in the board attachment part.

5. The X-ray CT apparatus according to claim 4, wherein the shielding part is disposed in a gap of the sub-detector modules.

6. The X-ray CT apparatus according to claim 1, further comprising:

a support block that supports the sub-detector modules, wherein the support block includes a material having a relatively large thermal conductivity.

7. The X-ray CT apparatus according to claim 1, wherein the plurality of tiling modules is arranged in at least one of the channel direction or the body axis direction of the subject.

* * * * *